United States Patent
Secrist et al.

(10) Patent No.: US 11,338,565 B2
(45) Date of Patent: May 24, 2022

(54) METHOD FOR IMPROVING CREEP PERFORMANCE IN ELASTIC APPLICATIONS

(71) Applicant: Bostik, Inc., Wauwatosa, WI (US)

(72) Inventors: Kimberly E. Secrist, Wauwatosa, WI (US); Ronald F. Graf, South Milwaukee, WI (US)

(73) Assignee: Bostik, Inc., Wauwatosa, WI (US)

( * ) Notice: Subject to any disclaimer, the term of this patent is extended or adjusted under 35 U.S.C. 154(b) by 0 days.

(21) Appl. No.: 15/586,673

(22) Filed: May 4, 2017

(65) Prior Publication Data

US 2017/0361597 A1 Dec. 21, 2017

Related U.S. Application Data

(60) Provisional application No. 62/332,819, filed on May 6, 2016.

(51) Int. Cl.
*B32B 37/12* (2006.01)
*B05C 5/02* (2006.01)
(Continued)

(52) U.S. Cl.
CPC ........ *B32B 37/1207* (2013.01); *A61L 15/225* (2013.01); *A61L 15/585* (2013.01);
(Continued)

(58) Field of Classification Search
CPC .................................................. B32B 37/1207
See application file for complete search history.

(56) References Cited

U.S. PATENT DOCUMENTS

| 4,626,305 A | 12/1986 | Suzuki et al. |
| 4,687,477 A | 8/1987 | Suzuki et al. |

(Continued)

FOREIGN PATENT DOCUMENTS

| CN | 1380050 A | 11/2002 |
| CN | 1689710 A | 11/2005 |

(Continued)

OTHER PUBLICATIONS

Allegro Elastic Coating Nozzle, basic setup guidelines—provided by Applicant (Year: 2015).*

(Continued)

*Primary Examiner* — Daniel H Lee
(74) *Attorney, Agent, or Firm* — Christopher R. Lewis (57) ABSTRACT

A method and system of using a polyolefin-based, hot melt adhesive improves creep performance of elastic strands adhered to another substrate. Some deflection, greater than 1°, of the exit angle formed by a line normal to the axis of a neutrally-positioned applicator and the elastic strand extending from the applicator is introduced. Preferably, deflection of the entrance angle is also introduced and a head tilt angle is also provided. The use of deflection improves creep performance or allows for a reduced amount of adhesive to be used to achieve the same or similar creep performance. The elastic strands may be used to form a leg cuff in personal care products, such as diapers, and the substrate to which they are applied could be a polyethylene film or non-woven materials.

14 Claims, 3 Drawing Sheets

(51) Int. Cl.
  A61L 15/22 (2006.01)
  A61L 15/58 (2006.01)
  B32B 37/00 (2006.01)
  C09J 145/00 (2006.01)

(52) U.S. Cl.
  CPC ........ B05C 5/0241 (2013.01); B32B 37/0053 (2013.01); C09J 145/00 (2013.01); *B32B 2037/1215* (2013.01)

(56) References Cited

U.S. PATENT DOCUMENTS

| | | | |
|---|---|---|---|
| 4,815,660 | A | 3/1989 | Boger |
| 5,190,606 | A | 3/1993 | Merkatoris et al. |
| 6,136,371 | A | 10/2000 | Fidan et al. |
| 6,582,518 | B2 | 6/2003 | Riney |
| 7,052,548 | B2 | 5/2006 | Jones |
| 8,551,276 | B2 | 10/2013 | Rothen |
| 9,168,554 | B2 | 10/2015 | Saine et al. |
| 2009/0000545 | A1 | 1/2009 | Bolyard, Jr. et al. |
| 2012/0258246 | A1* | 10/2012 | Saine ............ B05B 7/0815 427/207.1 |
| 2014/0235127 | A1 | 8/2014 | DeJesus et al. |
| 2015/0024649 | A1* | 1/2015 | Czaplewski ........ C09J 123/12 442/328 |
| 2015/0147461 | A1 | 5/2015 | Lessley et al. |
| 2017/0204306 | A1 | 7/2017 | Wang et al. |

FOREIGN PATENT DOCUMENTS

| | | | |
|---|---|---|---|
| DE | 29905090 | 3/1999 | |
| DE | 29905090 U1 | 3/1999 | |
| DE | 29905090 | 7/1999 | |
| DE | 29905090 U1 | 7/1999 | |
| EP | 713729 | 5/1996 | |
| EP | 0713729 A1 * | 5/1996 | .......... B05C 5/0279 |
| GB | 2148183 | 5/1985 | |
| WO | WO2004094073 | 11/2004 | |
| WO | WO-2004094073 A1 * | 11/2004 | .......... B05C 5/0245 |
| WO | WO2011128439 | 10/2011 | |
| WO | 2014014491 A1 | 1/2014 | |

OTHER PUBLICATIONS

Allegro(TM) Elastic Attachment Nozzle. Nordson Corporation. Jun. 2012 (Year: 2012).*
Allegro Elastic Coating Nozzle. Nordson Corporation. 2012 (Year: 2012).*
Universal(TM) Allegro(TM) Elastic Coating Nozzels. Nordson Corporation. Feb. 2015. [retrieved on Jun. 30, 2017] Retrieved from the Internet. <URL: http://emanuals.nordson.com/adhesives/English_ Manuals/1120705.pdf>.
ITW Dynatec. Layout, 1-Port Ultra Applicator. Drawing No. 120474 Rev. A. Mar. 4, 2016.
Allegro Elastic Coating Nozzle, Basic Setup Guidelines. 2015.
Extended European Search Report, dated Apr. 12, 2019.
Chinese Search Report dated Aug. 24, 2020.

* cited by examiner

METHOD FOR IMPROVING CREEP PERFORMANCE IN ELASTIC APPLICATIONS

CROSS-REFERENCE TO RELATED APPLICATION

This application claims priority under 35 U.S.C. § 119 to U.S. Patent Application No. 62/332,819, filed on May 6, 2016.

FIELD OF INVENTION

This invention relates to methods for using a polyolefin-based adhesive to bond elastic strands to substrates. More particularly, the invention is especially advantageous in improving creep performance of an elastic strand adhered to non-woven materials or thermoplastic films that are often seen in manufacturing a variety of disposable, nonwoven hygienic products such as baby diapers, adult incontinent articles, and feminine hygiene pads.

BACKGROUND OF THE INVENTION

Hot melt adhesives typically exist as a solid mass at ambient temperature and can be converted to a flowable liquid by the application of heat. These adhesives are particularly useful in manufacturing a variety of disposable goods where bonding of various substrates is often necessary. Specific applications include disposable diapers, hospital pads, feminine sanitary napkins, pantyshields, surgical drapes and adult incontinent products, collectively known as disposable nonwoven hygienic products. Other diversified applications have involved paper products, packaging materials, automotive headliners, appliances, tapes and labels. In most of these applications, the hot melt adhesive is heated to its molten state and then applied to a substrate, often named as the primary substrate. A second substrate, often named as the secondary substrate, is then immediately brought into contact with and compressed against the first. The adhesive solidifies on cooling to form a strong bond. A major advantage of hot melt adhesives is the absence of a liquid carrier, as would be the case of water or solvent based adhesives, thereby eliminating the costly process associated with solvent removal.

For many applications, hot melt adhesives are often extruded directly onto a substrate in the form of a thin film or a bead by using piston or gear pump equipment. In this case, the substrate is brought into intimate contact with a hot die under pressure. The temperature of the die must be maintained well above the melting point of the adhesive to allow the molten hot melt material to flow through the application nozzle smoothly. For most applications, particularly those encountered in food packaging and disposable nonwovens hygienic article manufacturing, bonding of delicate and heat sensitive substrates, such as thin gauge plastic films, is often involved. This imposes an upper limit on coating temperature for hot melt adhesive applications. Today's commercial hot melts are typically formulated to have coating temperatures below 200° C., preferably below 150° C. to avoid substrate burning or distortion. Besides direct coating, several indirect or noncontact coating methods, through which a hot melt adhesive can be spray coated with the aid of compressed air onto a substrate from a distance, are also developed. These non-contact coating techniques include conventional spiral spray, Omega™, Surewrap™ and various forms of melt-blown methods. The indirect method, however, requires that the viscosity of the adhesives must be sufficiently low, usually in the range of 500 to 30,000 mPa·s, preferably in the range of 500 to 15,000 mPa·s, at the application temperature in order to obtain an acceptable coating pattern. The low viscosity required to maintain sprayability in such systems leads to compromised performance as such systems require the use of low polymer levels or polymers with low molecular weight that lead to the adhesive displaying poor cohesive strength. Many other physical factors, especially the rheological properties of the adhesive, come into play in determining the sprayability of a hot melt. The majority of commercial hot melt products do not lend themselves to spray applications. There are no accepted theoretical models or guidelines to predict sprayability and it must be determined empirically with application equipment.

Hot melt adhesives are organic materials typically consisting of a polymer, a plasticizer, a tackifying resin and an antioxidant package. Other ingredients, such as wax, filler, colorant and UV absorber, can also be used to modify the adhesive properties or to provide special attributes. These organic ingredients are prone to heat degradation under the coating conditions of the adhesive. For example, the widely used commercial hot melt adhesive based on styrene-isoprene-styrene (SIS) triblock copolymer, when subjected to 175° C. for 24 hours, can suffer from a viscosity drop of about 50 percent from its original value. A styrene-butadiene-styrene (SBS) based hot melt may cause problems by crosslinking under similar conditions. Crosslinking can result in a dramatic increase in viscosity and may eventually render the adhesive un-flowable by the formation of a three dimensional polymer network. The viscosity change is often accompanied by charring, gelling, and formation of skin on top of the molten material. The degradation will inevitably lead to deterioration of the adhesive properties and performance. In addition, they can also cause equipment damage. The rate of degradation is temperature dependent; with a higher temperature, the rate of degradation increases. Thus, reducing the coating temperature of the adhesive can slow down degradation.

There is a desire in the industry to switch to direct strand coating processes to allow for increased line speeds; additionally, a need exists to switch away from styrene block copolymer (SBC)-type formulations to materials with less odor and/or which are more thermally stable, such as polyolefin hot-melt systems. When operating under known coater configurations for a direct strand coat process, however, current polyolefin-type materials often show inadequate and inconsistent end performance. Creep retention—the ability of the adhesive to hold an elastic strand to at least one non-woven substrate or polymeric film—is particularly compromised during long-term aging of polyolefin-containing formulations.

SUMMARY OF THE INVENTION

The current invention addresses the need for hot melt adhesives that can be applied at high production line rates and display enhanced stability towards heat and shear while providing consistently high levels of creep performance. This invention describes optimized process configurations to improve ultimate creep performance when directly applying adhesives to elastic strands. The methods outlined herein are directed to employing polyolefin-containing adhesive formulations. This invention solves the problem of maintaining adequate end performance criteria with process and substrate changes without having to change formulations. Most notably, this invention allows for lower amounts of adhesive to be used without losing performance. Enabling lower add-ons can potentially allow customers to use thinner substrates.

The invention pertains to the process of direct elastic strand coating. Particularly, this invention discloses methods to carefully control the path of the elastic strand through judicious placement of the applicator head, idlers, rollers, and strand guides. Overall, the process is designed to create a downward force on the elastic strands at the point of adhesive application; this downward force forms an exit angle, either alone or along with an entrance angle, both of which can be individually adjusted to optimize end-use performance using hot-melt adhesive formulations based on polyolefins and mixtures thereof.

According to an embodiment of the present invention, a method of using a polyolefin-based, hot melt adhesive comprises the steps of: applying the adhesive in a molten state with an applicator to a primary substrate comprising an elastic strand, wherein an exit angle defined by a line normal to the axis of a neutrally-positioned applicator and the elastic strand extending from the applicator in the downstream direction of travel is at least 1° and bonding a secondary substrate to the first substrate by contacting the secondary substrate with the adhesive. Optionally, the method of the invention further comprises, during the applying step, providing an entrance angle defined by a line normal to the axis of a neutrally-positioned applicator and the elastic strand extending from the applicator in the upstream direction of travel that is at least 1°. According to a further embodiment of the invention, during the applying step, a head tilt angle defined by a line tangent to the point of contact of the strand and the applicator tip and an axial line extending along the direction of travel of the adhesive as it exits the applicator is provided over a range of between 60° and 89° or between 91° and 120°.

According to another embodiment of the present invention, a system for applying a polyolefin-based, hot melt adhesive to an elastic strand comprises an applicator having an applicator tip and an outlet roller or idler disposed above the vertical position of the applicator tip. The applicator tip is adapted to contact a linearly moving primary substrate comprising an elastic strand and adapted to apply the adhesive to the primary substrate. The outlet roller or idler is disposed to provide an exit angle defined by a line normal to the axis of a neutrally-positioned applicator and the elastic strand extending from the applicator in the downstream direction of travel of at least 1°. The system of the invention may further comprise an inlet roller or idler configured above the vertical position of the applicator tip to provide an entrance angle defined by a line normal to the axis of a neutrally-positioned applicator and the elastic strand extending from the applicator in the upstream direction travel of at least 1°. The applicator may be configured to provide a head tilt angle defined by a line tangent to the point of contact of the strand and the applicator tip and an axial line extending along the direction of travel of the adhesive as it exits the applicator of between 60° and 89° or between 91° and 120°.

An embodiment of the invention also includes the system of the invention along with a polyolefin-based, hot melt adhesive (as described herein) contained in the application.

In accordance with an embodiment of the present invention, the polyolefin-based, hot melt adhesive comprises a polymer component which is a polyolefin blend of propylene polymers produced using single-site catalysts (SSC); a high molecular weight essentially amorphous polypropylene polymer (HMW SSC-PP polymer) and a low molecular weight semicrystalline polypropylene copolymer (LMW SSC-PP polymer). The distinct molecular weights of the component polymers give rise to a polymer blend having a bimodal molecular weight distribution. Besides the difference in molecular weights, the SSC-PP polymer in the blend also differs in enthalpy of melting, which is an indirect measure of polymer crystallinity. For the purposes of the present invention, the LMW semicrystalline SSC-PP polymer is defined as propylene homo- or co-polymers having a weight average molecular weight (Mw) of 100,000 g/mole or less, a distinct melting point on the DSC curve and an enthalpy of melting above 30 Joules per gram of material (J/g). The HMW essentially amorphous SSC-PP polymer is defined as propylene homo- or copolymers having a weight average molecular weight (Mw) above 100,000 g/mole, and containing a small fraction of residue crystallinity that is characterized by a small, but noticeable melting point on a DSC curve with an enthalpy of melting below 30 Joules per gram of material (J/g). The said HMW essentially amorphous SSC-PP polymer may also be completely amorphous showing no melting peak on its DSC curve. The composition also includes a tackifier component, a plasticizer component, an antioxidant package, and optionally other additives such as a wax, a filler, a colorant, a UV absorber, and another polymer. The composition is well suited for applications with a variety of direct and indirect coating methods and has a novel combination of properties including low coating temperature, wide coating temperature range, excellent adhesion to low surface energy plastic substrates, high cohesive strength, high shear resistance, high strand hold property, low viscosity, low melting point and superior heat stability. The composition of the present invention is particularly useful for food packaging, product assembly and for assembly of disposable nonwoven articles for bonding of polyethylene and polypropylene films, nonwoven fabrics and elastic strands to each other or to themselves.

As used herein, SSC refers to single-site catalysts for α-olefin polymerization.

As used herein, Mw refers to weight average molecular weight of a polymer.

For the purposes of the present invention, the term essentially amorphous is used to refer to a state wherein a polypropylene-based (PP) polymer exhibits an enthalpy of melting from 0 J/g to about 30 J/g.

For the purposes of the present invention, the term semicrystalline is used to refer to a state wherein a PP based polymer exhibits an enthalpy of melting above 30 J/g.

As used herein, HMW SSC-PP refers to a class of high molecular weight essentially amorphous propylene homopolymers or copolymers produced by using single-site catalysts having a Mw greater than about 100,000 g/mole. The said polymers can be completely amorphous showing no melting peaks on a DSC curve, but they can also have a small fraction of crystals that give rise on a DSC curve to a small, but noticeable melting peak or peaks with associated enthalpy of melting of 30 joules per gram of material (J/g), or less, i.e. from 0 J/g to about 30 J/g.

As used herein, DSC curve refers to a plot of heat flow or heat capacity versus temperature obtained by using differential scanning calorimetry (DSC) instrument. The test method used to determine these values is ASTM E793-01 "Standard. Test Method for Enthalpies of Fusion and Crystallization by Differential Scanning Calorimtry".

As used herein, LMW SSC-PP refers to a class of low molecular weight semicrystalline propylene homopolymers or copolymers having a weight average molecular weight (Mw) of about 100,000 g/mole or less, and a distinct melting peak or peaks on a DSC curve with associated enthalpy of melting of 30 joules per gram of material (J/g) or greater, i.e. typically from about 30 J/g to about 100 J/g. The terms "enthalpy of melting", "enthalpy of fusion", "heat of fusion" and "heat of melting" are used interchangeably.

As used herein, SSC-PP blend refers to a polymer blend comprising of at least one HMW SSC-PP polymer and at least one LMW SSC-PP polymer.

The hot melt adhesive composition used in connection with the present invention may comprise a polypropylene polymer blend containing a semicrystalline LMW SSC-PP PP polymer and an essentially amorphous HMW SSC-PP polymer with a ratio of the said LMW material to the said HMW material ranging from 9:1 to 1:9 parts by weight. The adhesive composition comprises, in addition to the said SSC-PP blend, a tackifying resin, a plasticizer and an antioxidant system as the primary ingredients. The compositions of the present invention have taken advantage of complimentary properties between the semicrystalline LMW SSC-PP polymer and the essentially amorphous HMW SSC-PP polymer and have overcome the shortcomings of the prior art polyolefin based hot melt adhesives. The composition of the present invention provides well balanced properties of tensile strength, toughness, flexibility and adhesion. It exhibits high bond strength to a variety of low surface energy substrates such as low density polyethylene (LDPE) and isotactic polypropylene (iPP) films, high cohesive strength to hold elastic materials under constant tension, excellent heat stability, good wet-out properties, broad application temperature range, long open time, good green bond strength, low viscosity, low or no residual tack when set, and suitability with essentially all known hot melt coating methods. In particular, the present invention leads to an adhesive composition that is well suited for a variety of spray coating application techniques, such as, for example, spiral spray, Omega™, Surewrap™, melt-blown, Control Coat®, and the like, and non-spray coating application techniques such as, for example, slot coat, V-slot™, Allegro™ and the like; these coating techniques are well known to those skilled in the art and are not a subject of discussion of the present invention.

The present invention may therefore be used with a hot melt adhesive composition comprising a polymer blend containing at least one semicrystalline LMW SSC-PP copolymer and at least one essentially amorphous HMW SSC-PP copolymer; both of which are either homopolymers of propylene or copolymers of propylene with an alpha-olefin comonomer prepared by using single-site catalysts (SSC) and have a statistically random comonomer distribution along the polymer chain. The weight ratios of the semicrystalline LMW SSC-PP polymer to the essentially amorphous HMW SSC-PP polymer in the blends ranges from 9:1 to 1:9 and the total amount of the polymer blend in the composition of the present invention is from 20% to 80% by weight, preferably from 30% to 60% by weight and most preferably from 30% to 50% by weight.

The present invention may be used with a hot melt adhesive composition containing the polymer blend herein mentioned above in combination with a plasticizer, a compatible tackifier and antioxidant. The composition can contain optional additives including, but not limited to, a wax, a functionalized polymer, a colorant, an UV absorber, and a filler.

A hot melt composition used with the present invention may comprise the polymer blend that has low viscosity ranging from 500 mPa·s to 35,000 mPa·s at 177° C., preferably from 1000 mPa·s to 20,000 mPa·s and most preferably from 2,000 mPa·s to 15,000 mPa·s. Low viscosity is essential for application involving various spray coating methods.

A hot melt adhesive composition used with the present invention may provide, for nonwoven elastic attachment applications, a creep retention of at least 80% or higher; a value of 80% is generally the minimum acceptable by disposable nonwoven hygienic article industry.

Another objective is to teach the art of applying the hot melt composition of the present invention by using various hot melt coating methods and to provide a method of bonding or laminating two or more substrates by first applying the said hot melt to the primary substrate and subsequently mating the said primary substrate to a secondary or additional substrates.

Another objective of the present invention is to provide a method using a hot melt adhesive composition that is particularly useful for various application in manufacturing of nonwovens hygienic absorbent articles including, but not limited to baby diapers, training pants, adult incontinent articles, feminine pads, panty liners, surgical gowns and poultry absorbent pads, the said composition having well balanced properties of tensile strength, toughness, flexibility and adhesion. It exhibits high bond strength to a variety of low surface energy substrates such as LDPE and iPP films, high cohesive strength to hold elastic materials under constant tension, excellent heat stability, good wet-out property, broad application temperature range, long open time, good green bond strength, low viscosity, low or no residual tack when set, and suitability with essentially all known hot melt coating methods.

Embodiments of the invention include providing any deflection (either through a non-zero exit angle, a non-zero entrance angle, a non-90 degree head tilt angle, or any combination thereof) effective to provide an improvement of creep retention of 10%, more preferably 20%, and most preferably 30%, over the creep retention values for the same substrate, formulation and test conditions without any deflection for both initial creep and four-week aged creep values held at 54.4° C.

BRIEF DESCRIPTION OF THE DRAWING

The invention is best understood from the following detailed description when read in connection with the accompanying drawing. Included in the drawing are the figures identified below.

DETAILED DESCRIPTION OF THE INVENTION

The invention is best understood from the following detailed description when read in connection with the accompanying drawing figures, which shows exemplary embodiments of the invention selected for illustrative purposes. The invention will be illustrated with reference to the figures. Such figures are intended to be illustrative rather than limiting and are included herewith to facilitate the explanation of the present invention.

Figure 1:
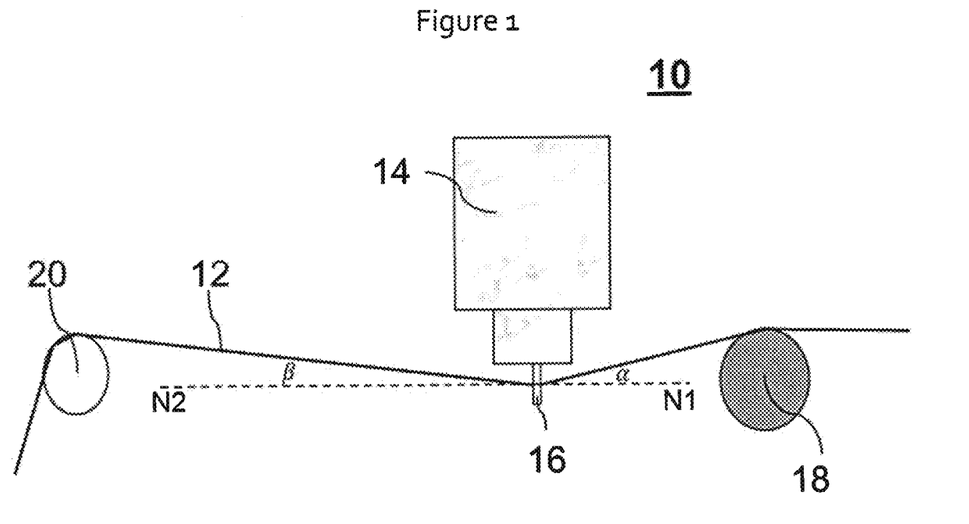
FIG. 1 is a schematic drawing showing a system according to the present invention having different entrance and exit angles greater than 1°.

FIG. 1 depicts a schematic drawing of a suitable set-up option showing an applicator head (or tip) forcing an elastic strand downward to create an entrance angle from the inlet strand guide to applicator head and an exit angle from the applicator head to first outlet idler/roller. While systems may have various configurations of guides (or idlers) and rollers, the inlet guide or roller discussed herein is the one closest to the applicator tip on the entrance side and the outlet guide or roller discussed herein is the guide or roller closest to the applicator tip on the exit side. Idler and guide are used synonymously herein. The entrance and exit angles are positive in that they extend upwardly as shown in the figures (or towards the applicator) from a line normal to the axis of a neutrally-positioned applicator.

More specifically, FIG. 1 shows an applicator system 10 for applying a polyolefin-based, hot melt adhesive to a primary substrate comprising an elastic strand 12 having different entrance and exit angles greater than 1°. System 10 comprises an applicator 14 having an applicator tip 16. Applicator 14 contains the adhesive in a molten state so that it can be delivered to elastic strand 12 and then hardened upon cooling in a known way. Applicator 14 has an applicator tip 16 adapted to contact elastic strand 12 which is moving linearly in operation, from left to right as shown in the figures. Tip 16 is adapted to apply the adhesive directly to the primary substrate. System 10 further comprises an outlet roller or idler 18 disposed above the vertical position of applicator tip 16 to provide an exit angle $\alpha$ defined by a line N1 normal to the axis of applicator 14 and the elastic strand extending from the applicator in the downstream direction of travel of at least 1°. More specifically, the vertical position of applicator tip 16 is defined by the point at which the applicator tip contacts elastic strand 12 and the vertical position of outlet roller or idler 18 is defined by the upper most point of contact with elastic strand 12. Exit angle $\alpha$ is shown in FIG. 1 along line N1, which extends horizontally from the point of contact of applicator tip 16 with elastic strand 12.

Line N1 extends horizontally in FIG. 1 because the system is oriented such that adhesive flows downwardly (in the absence of any head tilt), in general, from applicator 14 in use. As used herein, the entrance and exit angle are defined by the strand as it enters or exits the applicator tip, respectively, and a line normal to the axis of a neutrally-positioned applicator. A neutrally positioned applicator is one, such as shown in FIG. 1, whose axis is 90° from a line formed by an elastic strand having no entrance or exit angle (i.e., line N1 or N2 shown in FIG. 1). Systems other than that shown in the figures could be employed according to the present invention, such as application at an angle or sideways with the applicator disposed in its neutral position. For example, in a system which a neutrally-positioned applicator applies adhesive sideways (i.e., horizontally), then lines N1 and N2 would extend vertically. The "downstream direction of travel" is intended to mean the direction in which elastic strand 12 is traveling in operation of system 10, namely left-to-right as shown in the figures.

System 10 further comprises an inlet roller or idler 20 configured above the vertical position of applicator tip 16 to provide an entrance angle $\beta$ defined by a line normal to the axis of the applicator N2 and elastic strand 12 extending from the applicator in the upstream direction travel of at least 1°. More specifically, the vertical position of applicator tip 16 is defined by the point at which the applicator tip contacts elastic strand 12 and the vertical position of inlet roller or idler 20 is defined by the upper most point of contact with elastic strand 12. Entrance angle $\beta$ is shown in FIG. 1 along line N2, which extends horizontally from the point of contact of applicator tip 16 with elastic strand 12. The "upstream direction of travel" is intended to mean the direction opposite to which elastic strand 12 is traveling in operation of system 10, namely left-to-right as shown in the figures.

Commercially-available applicator systems for applying adhesive to an elastic strand and the applicator tips, or nozzles, for doing so include systems and products made by Nordson Corporation and ITW Dynatec, including the Nordson™ Zero-Cavity hot melt coating module with Allegro™ applicator tip and the ITW Dynatec Ultra™ Strand Coating System (SCS).

The various components of system 10 can be configured to modify entrance angle $\alpha$ and exit angle $\beta$. The specific values of the two angles may be optimized depending on a number of factors, including the adhesive formulation that is selected, the elastic material that is used, desired add-on weight of adhesive, line speed, creep retention desired, nozzle configuration, and processing conditions, among other known factors. Given the teachings of this invention and within known parameters, exit angle $\alpha$ may be between 1° and 20°, 20° and 10°, or 2.5° and 7.5°. Similarly, the entrance angle $\beta$ may be between 1° and 20°, 2° and 10°, or 2.5° and 7.5°. Although ranges are provided herein, each lower limit may extend to any disclosed upper limit, so that either the entrance or exit angle may extend from 1° to 7.5° or 2.5° to 20°, as examples. Furthermore, the invention contemplates utilizing only an exit angle and having no deflection on the entrance side (e.g., an entrance angle $\beta$ of 0°). Alternatively, the invention contemplates utilizing only an entrance angle and having no deflection on the exit side (e.g., an exit angle $\alpha$ of 0°).

Figure 2A:
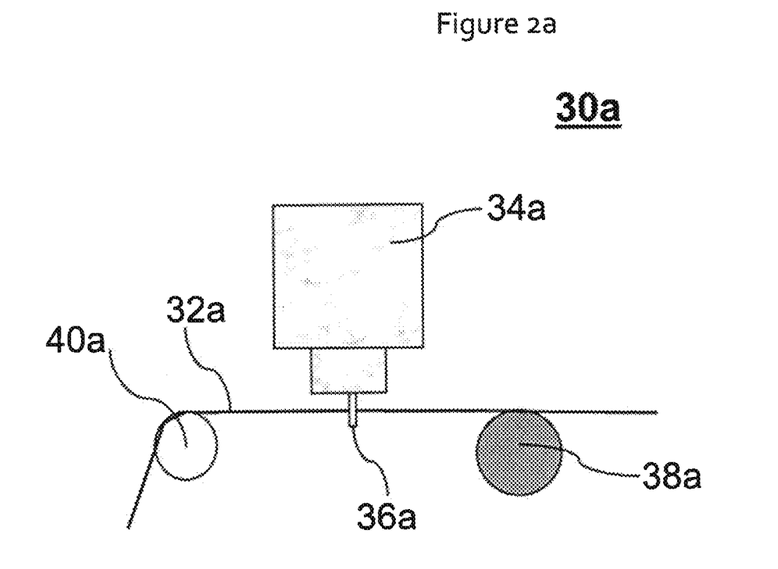
FIG. 2a is a schematic drawing showing a system according to the prior having no deflection of the entrance and exit angles.

FIG. 2a shows an embodiment according to a prior art system in which inlet roller or idler 40a and outlet roller or idler 38a are in the same vertical position as applicator tip 36a. More specifically, the upper most portions of where the two rollers or idlers contact elastic strand 32a are at the same vertical position as the point where applicator tip 36a contacts elastic strand 32a. Therefore, elastic strand 32a forms an essentially horizontal line from inlet roller or idler 40a to outlet roller or idler 38a, with no deflection. This horizontal line is normal relative to the axis of the applicator. Stated another way, both the entrance and exit angles are 0°. In this embodiment, applicator tip 36a is touching elastic strand 32a but is not exerting any downward force. This schematic could also be representative of indirect contact in which the applicator tip is not in contact with the elastic strand.

Figure 2B:
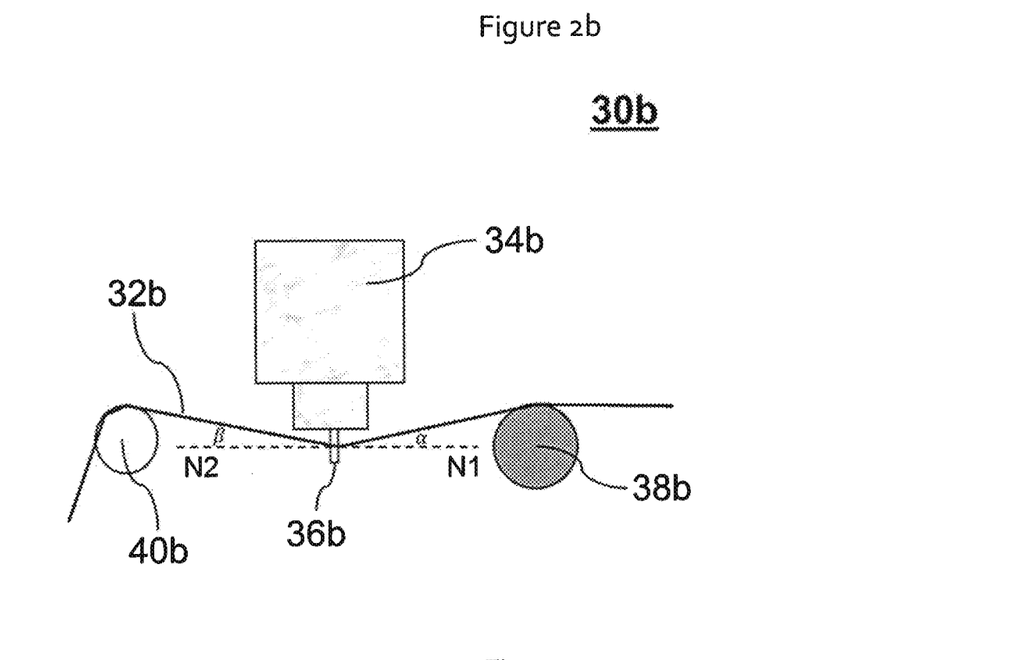
FIG. 2b is a schematic drawing showing a system according to the present invention having entrance and exit angles greater than 1°.

Alternative embodiments of the invention are shown in FIGS. 3b through 4b. In the embodiment shown in FIG. 2b, the components of system 30b are configured such that exit angle $\alpha$ and entrance angle $\beta$ are identical. In particular, inlet roller or idler 40b and outlet roller or idler 38b are the same distance and at the same vertical height relative to applicator tip 36b. As in other embodiments, when referring to vertical height, reference is being made to the upper most portion of where a roller or idler contacts elastic strand 32b. Similarly, the specific point of applicator tip 36b referred to is where the applicator tip contacts elastic strand 32b. In an alternative approach according to this embodiment, the two rollers might not be at the same vertical height and distance relative to applicator tip 36b, but they would be disposed such that exit angle α is equivalent to entrance angle β. For example, outlet roller or idler 38b could be at a lower vertical height and closer to applicator tip 36b, so long as the upper most portion of where the outlet roller or idler contacts elastic strand 32b is along the line formed by elastic strand 32b shown in FIG. 2b, such that exit angle α would be the same.

Figure 2C:
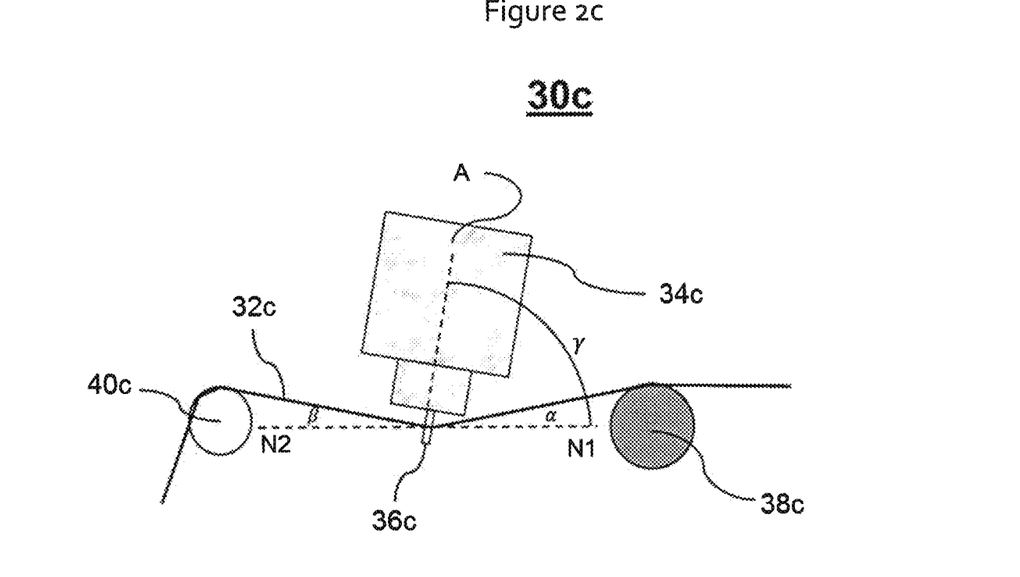
FIG. 2c is a schematic drawing showing a system according to the present invention having entrance and exit angles greater than 1° and a forward head tilt of the applicator.
Figure 3A:
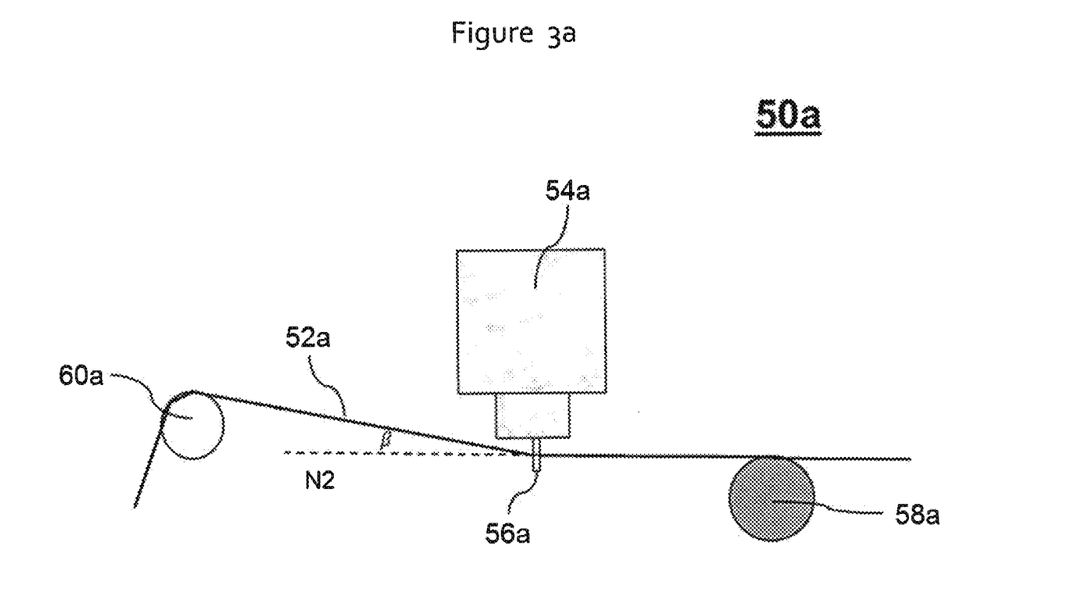
FIG. 3a is a schematic drawing showing a system according to the present invention having an entrance greater than 1° but no exit angle.
Figure 3B:
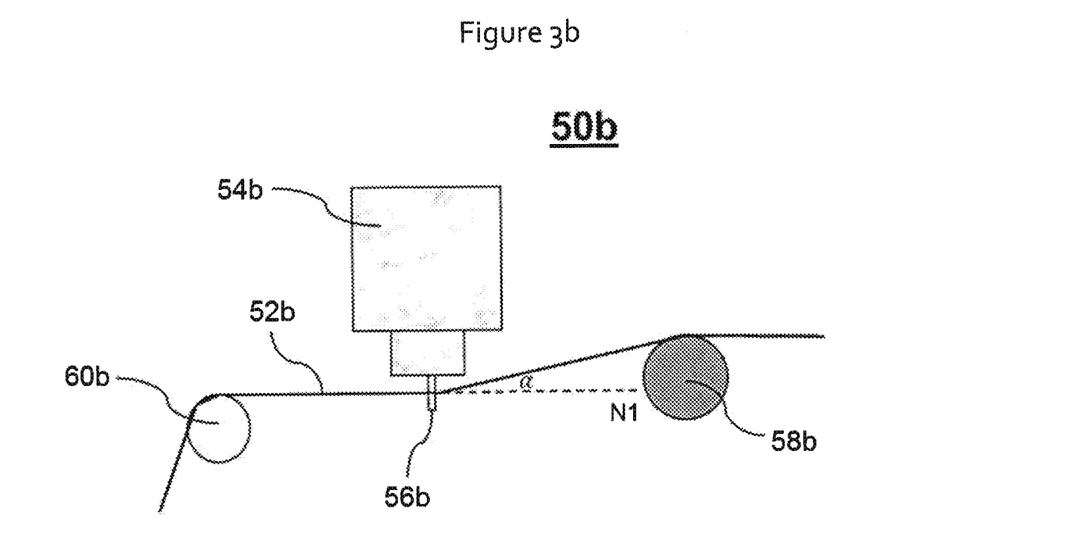
FIG. 3b is a schematic drawing showing a system according to the present invention having an exit greater than 1° but no entrance angle.

In the embodiment shown in FIG. 2c, the components of system 30c are configured such that, in addition to having an exit angle α and entrance angle β of at least 1°, a 'head tilt angle' γ of less than 89° exists. Known adjusting components can be used to adjust the head tilt of applicator 34c. The head tilt angle is defined by a line tangent to the point of contact of the strand and the applicator tip (extending from the point where applicator tip 36c contacts elastic strand 32c) and an axial line A extending along the direction of travel of the adhesive as it exits applicator tip 36c. (Line A is also the same line as the axis of the applicator.) The line tangent to the point of contact of the strand and the applicator tip will vary depending on the embodiment. For example, this line is congruent with the line formed by the strand at the inlet side of the applicator in cases where there is no entrance angle, such as in FIG. 2b. Similarly, this line is congruent with the line formed by the strand at the outlet side of the applicator in cases where there is no exit angle, such as in FIG. 2a. In cases where there is both an entrance and an exit angle, this line would be N1 or N2, as shown in FIG. 2c. In various systems, this line would extend in different directions. For example, in systems in which the application is done sideways (in the absence of head tilt), then the line tangent to the point of contact of the strand and the applicator tip would be a vertical line.

A 'forward' head tilt means that the head tilt angle is less than 89°, in that the head is tilting towards the downstream direction of travel of elastic strand 32c. In an alternative embodiment, a 'rearward' head tilt may be utilized, meaning that the head tilt angle is greater 91°. In alternative embodiments of the invention, the head tilt angle is between 60° and 89° or is between 91° and 120°. Preferably, the head tilt angle is between 70° and 88° and, more preferably, between 80° and 88°. Although ranges are provided herein, each lower limit may extend to any disclosed upper limit (for forward and rearward head tilts, separately), so that the head tilt angle may extend from 70° to 89°, as an example. The invention contemplates the use of a head tilt angle with no deflection of either the entrance or exit angle, with deflection of both, or with deflection of either the entrance or exit angle. Preferably, the system is configured to provide an entrance angle between 0.0° to 2.5° with an exit angle between 1.0° to 5.0° while the head tilt is between 75° to 90°. According to another embodiment, a head tilt of greater than 90° is provided with exit angles greater than 2.5°.

According to a further embodiment of the invention, a polyolefin-based, hot melt adhesive is applied one or more substrates to improve creep resistance of an elastic strand or other elastomeric component. A method according to an embodiment of the invention comprises applying the adhesive in a molten state with an applicator to a primary substrate comprising an elastic strand, wherein an exit angle defined by a line normal to the axis of a neutrally-positioned applicator and the elastic strand extending from the applicator in the downstream direction of travel is at least 1°. The method further comprises bonding a secondary substrate to the first substrate by contacting the secondary substrate with the adhesive. During the applying step, an entrance angle defined by a line normal to the axis of a neutrally-positioned applicator and the elastic strand extending from the applicator in the upstream direction of travel is formed of at least 1°. Such an entrance angle may be used as an alternative to, or in addition to, the exit angle of at least 1°. Also during the applying step, a head tilt angle is defined by a line tangent to the point of contact of the strand and the applicator tip and an axial line extending along the direction of travel of the adhesive as it exits the applicator of between 60° and 89° or between 91° and 120°. Such a head tilt angle may be used in addition to either or both of the non-zero entrance or exit angles or as an alternative to both. The preferred ranges discussed above in connection with the system equally apply to the method.

In an embodiment of the invention, a method of making a laminate comprises the steps of: (1) applying the hot melt adhesive composition of the invention in a molten state to a primary substrate using at least one of a non-zero entrance or exit angle or a head tilt angle not equal to 90°; and (2) bonding a secondary substrate to the first substrate by contacting the secondary substrate with the adhesive composition. The primary substrate may be an elastic portion of a diaper, such as an elastic strand used as part of a leg cuff of a diaper. Such elastic strands (or bands) and their application as part of a leg cuff of a diaper are shown in U.S. Pat. No. 5,190,606, incorporated herein by reference. The secondary substrate may comprise a nonwoven material or a film, such as a SMS nonwoven fabric polyethylene film, and the method may include folding the secondary substrate around the elastic strand. In this way, only the secondary substrate may serve as the substrate which encapsulates the strand or strands of the leg cuff. In an alternative embodiment, a tertiary substrate is used, and the secondary and tertiary substrates may be mated to the elastic strand on opposite sides of the elastic strand. In such an embodiment, the secondary substrate may be a polyethylene film and the tertiary substrate may be a film of nonwoven material, or verse visa. Furthermore, a composite diaper backsheet consisting of a polyolefin film joined to a nonwoven fabric can also be used as the secondary and tertiary substrates mentioned above.

As indicated above, the adhesive comprises a polymer component, a plasticizer, a tackifying resin and an antioxidant package, and the polymer component comprises a polyolefin. Thus, the adhesive of the present invention is polyolefin based, although this does not exclude small amounts of non-polyolefin constituents, such as less than 49% by weight, more preferably less than 25% by weight, more preferably less than 10% by weight, and most preferably less than 5% by weight. Preferably, the polymer component comprises at least 50% by weight of polyolefin, more preferably 51%, more preferably 75%, even more preferably 90%, still more preferably 95%, and most preferably all or substantially all polyolefin. The polymer component may comprise polyolefins or a blend of polyolefins or may consist essentially of a polyolefin or a blend of polyolefins or may consist of a polyolefin or a blend of polyolefins. Some exemplary polyolefin-based adhesives suitable for use in connection with the present invention include those disclosed in US 2015/0024649 A1, incorporated herein by reference. Preferably, the polymer component is a heterophasic polyolefin, such as Borealis random heterophasic copolymers—referred to as RAHECO—which represent a special class of polypropylene (PP) impact copolymers. These materials have similar chemical compositions and phase structures as the general commercial impact copolymers, but possess improved compatibility between the crystalline PP matrix phase and the rubbery phase. Stemming from their unique production processes, RAHECO grades are proposed to be composed of a "soft" yet more crystalline, higher melting rubber phase in a crystalline PP matrix that can be adjusted over a wider range than typical commercial impact copolymer (ICP) systems. Additionally, the polymer can be a polypropylene impact copolymer available from LyondellBasell. Heterophasic polymers can be defined as multiple phase polymers, containing both continuous and discontinuous polymer phases. The continuous phase can also be referred to as the matrix phase and the discontinuous phase known as the rubber or elastomeric phase. The polyolefin blend described in U.S. Patent Application No. 62/278,747, filed on Jan. 14, 2016, is especially well-suited for use with the present invention, and aspects of it are described herein.

According to embodiments of the invention, the polyolefin component may be selected from the group consisting of polypropylene homopolymers, polypropylene copolymers, amorphous polyalpha-olefins (APAOs), olefin block copolymers, random heterophasic copolymers (which may be propylene-based), ethylene alpha-olefin copolymers, and ethylene copolymers, such ethylene vinyl acetate.

The compatible tackifying resins or tackifiers used in the hot melt adhesives used with the present invention are those which extend adhesive properties and improve specific adhesion. As used herein, the term "tackifying resin" includes:

(a) aliphatic and cycloaliphatic petroleum hydrocarbon resins having Ring and Ball softening points of from 10° C. to 150° C., as determined by ASTM method E28-58T, the later resins resulting from the polymerization of monomers consisting primarily of aliphatic and/or cycloaliphatic olefins and diolefins; also included are the hydrogenated aliphatic and cycloaliphatic petroleum hydrocarbon resins; examples of such commercially available resins based on a C5 olefin fraction of this type are Piccotac 95 tackifying resin sold by Eastman Chemicals and Escorez 1310LC sold by ExxonMobil Chemical Company and examples of hydrogenated cycloaliphatic petroleum hydrocarbon resins based on cyclopentadiene are Escorez 5400 from Exxonmobil and Resinall R1095S from Resinall Corporation;

(b) aromatic petroleum hydrocarbon resins and the hydrogenated derivatives thereof; an example of hydrogenated aromatic hydrocarbon resin is Arkon P-115 from Arakawa Chemicals;

(c) aliphatic aromatic petroleum derived hydrocarbon resins and the hydrogenated derivatives thereof;

(d) aromatic modified cycloaliphatic resins and the hydrogenated derivatives thereof;

(e) polyterpene resins having a softening point of from about 10° C. to about 140° C., the latter polyterpene resins generally resulting from the polymerization of terpene hydrocarbons, such as the mono-terpene known as pinene, in the presence of Friedel-Crafts catalysts at moderately low temperatures; also included are the hydrogenated polyterpene resins;

(f) copolymers and terpolymers of natural terpenes, e.g. styrene/terpene, cc-ethyl styrene/terpene and vinyl toluene/terpene;

(g) natural and modified rosin such as, for example, gum rosin, wood rosin, tall-oil rosin, distilled rosin, hydrogenated rosin, dimerized rosin and polymerized rosin;

(h) glycerol and pentaerythritol esters of natural and modified rosin, such as, for example, the glycerol ester of pale wood rosin, the glycerol ester of hydrogenated rosin, the glycerol ester of polymerized rosin, the pentaerythritol ester of pale wood rosin, the pentaerythritol ester of hydrogenated rosin, the pentaerythritol ester of tall-oil rosin, and the phenolic modified pentaerythritol ester of rosin; and (i) phenolic-modified terpene resins such as, for example, the resin product resulting from the condensation in an acidic medium of a terpene and a phenol.

Mixtures of two or more of the above described tackifying resins may be required for some formulations. Although a range of about 15% to about 75% by weight tackifying resin may be used, the preferred amount is from about 30% to about 60% by weight. Tackifying resins which are useful for the present invention can perhaps include polar tackifying resins. However, the choice of available polar tackifying resins is limited in view of the fact that many of the polar resins appear only partially compatible with polyolefins.

As noted above, tackifying resins which are useful within the scope of the present invention comprise about 15% to about 75% by weight, preferably about 30% to about 60% by weight, of the composition. Preferably, the tackifying resins can be selected from any of the nonpolar types, which are commercially available. Preferred resins are aliphatic petroleum hydrocarbon resins and most preferred are nonpolar products such as hydrogenated dicyclopentadiene (HDCPD) or aromatically modified derivatives thereof with softening points above 70° C. Examples of such resins are Escorez 5400 and Escorez 5600 sold by ExxonMobil Chemical company.

A plasticizer can be present in the composition used with the present invention in amounts of about 1% to about 35% by weight, preferably from about 2% to about 20% by weight, in order to provide desired viscosity control and to impart flexibility. A suitable plasticizer may be selected from the group which includes the usual plasticizing oils, such as mineral oil, but also olefin oligomers and low molecular weight polymers, as well as vegetable and animal oils and derivatives thereof. The petroleum derived oils which may be employed are relatively high boiling materials containing only a minor proportion of aromatic hydrocarbons. In this regard, the aromatic hydrocarbons should preferably be less than 30% and more particularly less than 15% of the oil, as measured by the fraction of aromatic carbon atoms. More preferably, the oil may be essentially non-aromatic. The oligomers may be polypropylenes, polybutenes, hydrogenated polyisoprenes, hydrogenated polybutadienes, or the like having average molecular weight between about 350 g/mole and about 10,000 g/mole. Suitable vegetable and animal oils include glycerol esters of the usual fatty acids and polymerization products thereof. Other useful plasticizers can be found in the families of conventional dibenzoate, phosphate, phthalate esters, as well as esters of mono- or polyglycols. Examples of such plasticizers includes, but are not limited to dipropylene glycol dibenzoate, pentaerythritol tetrabenzoate, 2-ethylhexyl diphenyl phosphate, polyethylene glycol 4-di-2-ethylhexanoate; butyl benzyl phthalate, dibutyl phthalate and dioctylphthalate. The plasticizers that find usefulness in the present invention can be any number of different plasticizers but the inventors have discovered that mineral oil and liquid polybutenes having average molecular weight less than 5,000 are particularly advantageous. As will be appreciated, plasticizers have typically been used to lower the viscosity of the overall adhesive composition without substantially decreasing the adhesive strength and/or the service temperature of the adhesive as well as to extend the open time and to improve flexibility of the adhesive.

Waxes can be used to reduce the melt viscosity of the hot melt adhesive composition. Although amounts varying from about 0% to about 20% by weight may be used in the composition of the present invention, the preferred amounts are between about 0% to about 15% by weight. These waxes can also effect the set-up time and the softening point of the adhesive. Among the useful waxes are:

1. low molecular weight, that is, number average molecular weight (Mn) equal to 500-6000 g/mole, polyethylene having a hardness value, as determined by ASTM method D-1321, from about 0.1 to 120, having an ASTM softening point from about 65° C. to 140° C.;
2. petroleum waxes such as paraffin wax having a melting point from about 50° C. to 80° C. and microcrystalline wax having a melting point from about 55° C. to 100° C., the latter melting points being determined by ASTM method D127-60;
3. synthetic waxes made by polymerizing carbon monoxide and hydrogen such as Fischer-Tropsch wax; and
4. polyolefin waxes. As used herein, the term "polyolefin wax" refers to those polymeric or long-chain entities comprised of olefinic monomer units. This type of materials are commercially available from Westlake Chemical corporation, 2801 Post Oak Blvd., Houston, Tex. under the tradename designation "Epolene" and from Honeywell Corporation, 101 Columbia Road, Morristown, N.J. under the trade name designation "A-C". The materials which are preferred for use in the composition of the present invention have a Ring and Ball softening point of from about 100° C. to 170° C. As should be understand, each of these wax diluents is solid the room temperature.

Other substances which include hydrogenated animal, fish and vegetable fats and oils such as hydrogenated tallow, lard, soya oil, cottonseed oil, castor oil, menhaden oil, cod liver oil, and the like, and which are solid at the room temperature by virtue of their being hydrogenated, are also useful with respect to functioning as a wax diluent equivalent. These hydrogenated materials are often referred to in the adhesive industry as "animal or vegetable waxes".

The adhesive used with present invention may include a stabilizer in an amount of from about 0.1% to about 3% by weight. Preferably from about 0.2% to 1% of a stabilizer is incorporated into the composition. The stabilizers which are useful in the hot melt adhesive compositions of the present invention are incorporated to help protect the polymers noted above, and thereby the total adhesive system, from the effects of thermal and oxidative degradation which normally occurs during the manufacture and application of the adhesive as well as in the ordinary exposure of the final product to the ambient environment. Among the applicable stabilizers are high molecular weight hindered phenols and multifunctional phenols, such as sulfur and phosphorous-containing phenols. Hindered phenols are well known to those skilled in the art and may be characterized as phenolic compounds that also contain sterically bulky radicals in close proximity to the phenolic hydroxyl group thereof. In particular, tertiary butyl groups generally are substituted onto the benzene ring in at least one of the ortho positions relative to the phenolic hydroxyl group. The presence of these sterically bulky substituted radicals in the vicinity of the hydroxyl group serves to retard its stretching frequency and correspondingly, its reactivity; this steric hindrance thus providing the phenolic compound with its stabilizing properties. Representative hindered phenols include:

1,3,5-trimethyl-2,4,6-tris(3-5-di-tert-butyl-4-hydroxybenzyl) benzene;
pentaerythritol tetrakis-3(3,5-di-tert-butyl-4-hydroxyphenyl) propionate;
n-octadecyl-3(3,5-di-tert-butyl-4-hydroxyphenyl) propionate;
4,4'-methylenebis(4-methyl-6-tert butylphenol);
2,6-di-tert-butylphenol;
6-(4-hydroxyphenoxy)-2,4-bis(n-octylthio)-1,3,5-triazine;
2,3,6-tris(4-hydroxy-3,5-di-tert-butyl-phenoxy)-1,3,5-triazine;
di-n-octadecyl-3,5-di-tert-butyl-4-hydroxybenzylphosphonate;
2-(n-octylthio)ethyl-3,5-di-tert-butyl-4-hydroxybenzoate; and
sorbitol hexa-3(3,5-di-tert-butyl-4-hydroxy-phenyl) propionate.

The performance of these stabilizers may be further enhanced by utilizing, in conjunction therewith; (1) synergists such as, for example, thiodipropionate esters and phosphites; and (2) chelating agents and metal deactivators as, for example, ethylenediaminetetraacetic acid, slats thereof, and disalicylalpropylenediimine.

It should be understood that other optional additives may be incorporated into the adhesive composition used with the present invention in order to modify particular physical properties. These may include, for example, such materials as inert colorants e.g. titanium dioxide, fillers, fluorescent agents, UV absorbers, surfactants, other types of polymers, etc. Typical fillers include talc, calcium carbonate, clay silica, mica, wollastonite, feldspar, aluminum silicate, alumina, hydrated alumina, glass microspheres, ceramic microspheres, thermoplastic microspheres, baryte and wood flour. Surfactants are particularly important in hygienic disposable nonwoven because they can dramatically reduce the surface tension, for example, of the adhesive applied to diaper core, thereby permitting quicker transport and subsequent absorption of urine by the core. Additional suitable additives include nucleating and/or clarifying agents.

The adhesive composition of the present invention may be used as a general purpose hot melt adhesive in a number of applications such as, for example, in disposable nonwoven hygienic articles, paper converting, flexible packaging, wood working, carton and case sealing, labeling and other assembly applications. Particularly preferred applications include nonwoven disposable diaper and feminine sanitary napkin construction, diaper and adult incontinent brief elastic attachment, diaper and napkin core stabilization, diaper backsheet lamination, industrial filter material conversion, surgical gown and surgical drape assembly, etc.

The resulting hot melt adhesives may be then applied to substrates using a variety application technique. Examples includes hot melt glue gun, hot melt slot-die coating, hot melt wheel coating, hot melt roller coating, melt blown coating, spiral spray, contact or noncontact strand coatings branded as Omega™, Surewrap™, V-slot™ and Allegro™ methods and the like. In a preferred embodiment, the hot melt adhesive is directly applied onto elastic strands using the strand coating methods, which are a preferred technique for elastic attachment in diaper and adult incontinent article manufacturing. In one example, the hot melt composition of the present invention is coated using Allegro™ nozzle to form a continuous adhesive bond line on elastic strands used for elasticized legs, leg cuffs and waistbands on baby diapers, training pants and adult incontinent articles. It is not the intent of this invention to provide a full description of various techniques and the details can be found in the literature or on nozzle manufacturer's websites www.nordson.com or www.itw.com.

In summarizing the invention, the applicator tip or head is lowered into the elastic strand during the coating process when running a polyolefin-based formulation. For background, the head height in direct strand applications is typically run such that it just barely touches the elastic strands employing SBc-based adhesives. This stems from observations that running with no contact results in glue not hitting the strands while using deep engagement results in adhesive "spitting" through the strands onto the substrate below. Ideally, the elastic strands go through a strand guide and experience a downward force from the applicator head pushing into the elastic strands creating an entrance angle (strand guide to applicator head). By positioning an idler or roller further downstream of the applicator head at a vertical position above the applicator, an additional angle is formed. This angle—defined here as the exit angle—can be between the applicator head and first idler/roller. The entrance and exit angle can be further tuned by adjusting the distance of the coating equipment relative to each other.

As customers continue efforts to downgauge the nonwoven and/or polymeric films used in elastic applications, the thermal energy of the adhesive at high add-on levels is more likely to lead to undesirable burn through of the substrates. In order to avoid damage to the substrates (compromising the final product), lower quantities of adhesive are required which can lead to significant drops in creep performance. The current invention allows lower add-on level to be used while maintaining adequate creep performance, thus making the process more suitable for low basis-weight substrates. The effect of the use of deflection according to the invention as applied to polyolefin-based adhesives was found to be surprising, especially when compared with the effect of deflection on adhesives based on styrene block copolymers. In the latter adhesives, either little or no improvement in creep retention was achieved through the use of deflection or the adhesives tended to agglomerate and coat the substrates unevenly upon deflection. This surprising effect is shown by comparing the examples of the invention set forth below with Comparative Examples 1 and 2.

Without being bound to any theory, it is proposed that inventive hot-melt adhesives exhibit higher flow under conditions where the elastic strands are intimately engaged with the application nozzle such as is the case when utilized under the "deflected" coating geometries defined in the specification. This ability appears to stein from the semi-crystalline nature of the polyolefins used in the inventive formulations which allows flow (high values of tan d, G"/G' values) to be maintained with stiffness (storage modulus, G') developing only slowly upon quench cooling. In comparison, "glassy" systems, such as those based on styrene block copolymers (SBc), are known to vitrify rapidly upon rapid cooling. It is proposed that these comparatively hard, less flowing materials cannot as readily withstand intense strand engagement ("deflection") at the point of application. In extreme cases, this leads to SBc-based adhesives being "split" by deflected strands and violently discharged from the target bonding area of the elastic component. By remaining in a relatively soft or gel like state (e.g. displaying tan d values >1) while being rapidly cooled, the inventive hot melt adhesive systems are proposed to withstand a higher degree of deformation allowing them to be more evenly coated under the conditions defined in the specification which, in turn, leads to improved initial and aged creep retention.

According to embodiments of the invention, at least some deflection is introduced, such as by: (1) providing a non-zero exit angle, preferably of at least 1° or any of the other exit angles disclosed herein; (2) providing a non-zero entrance angle, preferably of at least 1° or any of the other entrance angles disclosed herein; (3) providing a non-90 degree head tilt angle, preferably of between 60° and 89° or is between 91° and 120° or (4) any combination of any of the foregoing, effective to achieve an improvement of creep retention of 10%, more preferably 20%, and most preferably 30% over the creep retention values for the same substrate, formulation and test conditions without any deflection for both initial creep and four-week aged values held at 54.4° C.

It should be understood that the above described method is not limited to any particular step or sequence of steps.

EXAMPLES

Specimens for creep test is prepared using a customized coater/laminator equipped with a Nordson™ Zero-Cavity hot melt coating module which is designed to accommodate Surewxap™, Allegro™ and slot die tips. For the present invention, an Allegro™ tip is used to apply the present composition directly to Invista™ elastic strands having 680 Decitex (dtex) fineness. The tip has three separate adhesive nozzles or orifices 5 mm apart capable of coating three elastic strands simultaneously.

As used herein, decitex (abbreviated dtex) refers to the mass in grams per 10,000 meters of fiber length. It is a measure of fiber fineness in textile industry.

Creep Resistance test was carried out with laminated specimens as described in Table 2 though Table 4. A segment of the laminated specimen about 350 mm is stretched completely and is securely attached to a piece of rigid Polyglass board. A length of 300 mm is marked and the elastic strands are cut at the marks. The specimen is then placed in an air-circulating oven at 37.8° C. (100° F.). Under these conditions, the elastic strands under stretch can retract to a certain distance. The distance between the ends of the said elastic strands is measured after four hours. The ratio of the final length to the initial length, defined as Creep Retention and expressed in percentage (%), is a measure of the ability of the adhesive to hold the elastic strands (larger numbers are preferred). Similarly, aged Creep retention tests were conducted by aging laminated for a set period of time (one week, two weeks, four weeks, etc.) at 54.4° C. (130° F.). After the designated amount of time samples are brought to room temperature for at least 12 hours before the Creep Resistance test is carried out. Furthermore, Green Creep refers to the laminates being tested immediately off the coater line. The elastic strands are likewise cut, but left at room temperature for 30 minutes. At that point the length of strand movement is measured and recorded (smaller numbers are preferred).

As used in the Examples below:

Nyflex 222B is a mineral oil plasticizer purchased from Nynas USA Inc., 840 Gessner Road, Suite 540, Houston, Tex.

Sukorez SU-210 is a hydrogenated hydrocarbon tackifying resin produced by Kolon Chemicals.

Escorez 5615 is a hydrogenated aromatic modified cycloaliphatic hydrocarbon resin with a 118° C. softening point. It is available from ExxonMobil Chemical.

L-MODU S901 is a low modulus, controlled tacticity polypropylenes available from Idemitsu.

Vestoplast EP NC 702 is a propylene-rich copolymer available from Evonik.

Irganox 1010 antioxidant is pentaerythritol tetrakis(3-(3, 5-di-tert-butyl-4-hydroxyphenyl)propionate) available from BASF.

Clopay BR134 is a breathable PE film from Clopay Plastic Product Co., Inc., 8585 Duke Boulevard, Mason, Ohio.

SQN SB 15 gsm is a spunbond nonwoven fabric purchased from First Quality Nonwovens Inc., 121 N Rd, McElhattan, Pa.

Irganox 1010 is a hindered phenol antioxidant purchased from BASF Corporation, 100 Park Avenue, Florham, N.J.

Example 1

Table 1 below provides examples of two types of polyolefin-based formulations used in the deflection studies discussed below, namely APAO and heterophasic.

TABLE 1

|  | Ex1 | Ex2 | Ex3 |
| --- | --- | --- | --- |
| Oil[a] | 29.3 | 5.0 | 29.0 |
| Resin | 46.2[b] | 54.5[c] | 50.0[b] |
| Stabilizer[d] | 0.5 | 0.5 | 0.5 |
| Crystalline Polyolefin[e] | 15.2 | — |  |
| Olefin Block Copolymer[f] | 8.8 | — |  |
| Polypropylene homopolymer[g] | — | 15.0 |  |
| Amorphous poly-α-olefin[h] (APAO) | — | 25.0 |  |
| RAHECO (polyolefin)[i] |  |  | 16.5 |
| Wax[j] |  |  | 4.0 |

[a]Nynas Nyflex 222B Mineral Oil
[b]ExxonMobil Escorez 5615 Petroleum Hydrocarbon Resin
[c]Kolon Sukorez SU-210 Hydrogenated C5/Cyclic Hydrocarbon Resin
[d]Tris(2,4-di-tert-butylphenyl) phosphite antioxidant
[e]LyondellBasell Pro-fax EP501V (propylene-based impact copolymer)
[f]Dow Infuse 9807 Olefin Block copolymer
[g]Idemitsu Kosan L-MODU S901
[h]Evonik Vestoplast EP NC 702 (propene rich)
[i]Borealis SD 350 BAS
[j]Alphamin 104N (polyethylene wax)

The compositions in Table 1 represent weight percents that equal to a total of 100 percent.

Table 2 summarizes initial and aged creep retention performance of formulation Ex1 run at a line speed of 500 m/min with a coat weight of 35 mg adhesive/m strand at an open time of 0.15 seconds using 40 psi nip compression. Substrates utilized during fabrication include a breathable polyethylene film as the secondary substrate, 680 dtex Invista elastic strands (3 strands at 5 mm spacing elongated at 300% during application), and 15 gsm nonwoven as the secondary substrate. The distance from inlet strand guide to applicator head was the same as from the applicator head to the first outlet idler and was equal to 3.5". In this case, values for both the entrance angle (inlet strand guide to applicator head) and exit angle (applicator head to first outlet idler) are identical. All angles were measured using a digital angle sensor available from M-D Building Products, Inc.

TABLE 2

Effect of Deflection Angles on Performance of Ex1

| Entrance Angle, ° | Exit Angle, ° | Green Creep, mm | Initial Retention, % | 1 Wk Aged Retention, % | 4 Wk Aged Retention, % |
| --- | --- | --- | --- | --- | --- |
| 0.0 | 0.0 | 70-140 | 10.4 (7.9) | 0.0 (0.0) | 0.0 (0.0) |
| 2.5 | 2.5 | 5-50 | 20.6 (9.0) | 14.4 (5.9) | 22.5 (5.0) |
| 5.0 | 5.0 | 0-3 | 81.6 (10.5) | 74.7 (6.8) | 70.1 (14.4) |
| 7.5 | 7.5 | 0 | 84.7 (12.5) | 82.8 (4.9) | 77.4 (4.9) |

Note:
standard deviation values from creep retention data collected on multiple samples given in parenthesis in all tables Table 2 demonstrates that increased deflection angle improves the creep retention at essentially every time during the specimen's lifecycle. This was a surprising discovery since it was previously believed that green creep performance was primarily dominated by the adhesive's ability to set-up and develop modulus quickly enough to hold the elastic strands. The improved creep retention is maintained throughout the four-week aging process at 54.4° C.

Example 2

As described above, the deflection can be increased by lowering the applicator head. Adjusting the distance of the strand guide and idlers relative to leading to the applicator head can also be employed to independently control both entrance and exit deflection angles. The examples below refer describe the deflection in terms of both the entrance angle (inlet strand guide to applicator head) and the exit angle (applicator head to first exit idler). The additional study of Example 2 was done to investigate the effect of deflection when the entrance and exit angles were not identical. Table 3 summarizes results of these studies employing formulation Ex1. Runs were performed as described above but at a line speed of 1200 ft/min. Except where noted, the distance from inlet strand guide to applicator head was the same as from the applicator head to the first outlet idler and was equal to 3.5". The coat weight was 35 mg adhesive/m strand.

TABLE 3

Example 2 - Effect of Ex1 Formulation on Decoupled Entrance and Exit Angles

| Entrance Angle, ° | Exit Angle, ° | Green Creep, mm | Initial Retention, % | 1 Wk Aged Retention, % |
| --- | --- | --- | --- | --- |
| 5.0 | 0.0 | 0-10 | 33.9 (12.3) | 20.9 (10.2) |
| 0.0 | 0.0 | 0 | 63.0 (23.9) | 31.0 (18.1) |
| 5.0 | 5.0 | 0 | 93.6 (3.5) | 73.7 (12.4) |
| 5.0[a] | 5.0 | 0 | 92.8 (5.2) | 76.8 (6.6) |

[a]Distance from strand guide to applicator head to 10.5"; distance from applicator head to first idler is 2.5".

Table 3 further demonstrates the importance of a non-zero exit angle. When the entrance angle was raised to 5.0° and the exit angle left at 0° C., the creep performance was worse than having no deflection angle at all for the particular formulation tested. Additionally, greatly increasing the distance from the strand guide to the applicator head (leaving the elastic strands unsupported and potentially increasing strand vibration) did not negatively impact creep performance so long as the exit angle deflection was maintained (non-zero).

Example 3

Example 3 was done to assess creep retention performance of the Ex2 formulation run under conditions described above and a line speed of 500 m/min. The distance from inlet strand guide to applicator head was the same as the distance from the applicator head to the first outlet idler and was approximately equal to 3.5". Except as otherwise noted, the coat weight was 35 mg adhesive/m strand. Table 4 summarizes the results of Example 3.

TABLE 4

Deflection Effects on APAO-based Formulation Ex2

| Entrance Angle, ° | Exit Angle, ° | Green Creep, mm | Initial Retention, % | 1 Wk Aged Retention, % | 4 Wk Aged Retention, % |
|---|---|---|---|---|---|
| 0.0 | 0.0 | 0 | 86.4 (12.4) | 84.1 (11.1) | 46.9 (21.6) |
| 2.5 | 2.5 | 0 | 96.9 (0.5) | 96.4 (3.0) | 88.7 (4.8) |
| 5.0 | 5.0 | 0 | 98.6 (0.4) | 96.5 (0.5) | 96.5 (0.8) |
| 7.5[a] | 7.5 | 0 | 94.8 (2.5) | 88.9 (5.0) | 90.1 (2.6) |

[a]Coat weight decreased from 35 mg adhesive/m strand to 20 mg adhesive/m strand Example 4

Example 4 was run to assess creep retention of increased deflection of APAO-based formulations. While offering the most drastic improvement in creep retention for heterophasic polyolefin adhesive formulations of Ex1, increased deflection was also shown to minimize standard deviation values and facilitate lower coat weights to be used in APAO-based formulations. The distance from inlet strand guide to applicator head was the same as the distance from the applicator head to the first outlet idler and was approximately equal to 3.5". Except as otherwise noted, the coat weight was 35 mg adhesive/m strand.

TABLE 5

Deflection Effects on RAHECO-based Formulation Ex3

| Entrance Angle, ° | Exit Angle, ° | Head Tilt, ° | Initial Retention, % | 4 Week Aged Retention, % |
|---|---|---|---|---|
| 0.0 | 0.0 | 90, neutral | 22.1 (17.1) | 27.7 (15.5) |
| 2.5 | 2.5 | 90, neutral | 90.0 (6.7) | 68.8 (18.7) |
| 5.0 | 5.0 | 90, neutral | 96.2 (0.6) | 90.4 (2.1) |
| 0.0 | 0.0 | 75, forward | 26.2 (11.3) | 34.6 (16.8) |
| 2.5 | 2.5 | 75, forward | 91.0 (6.0) | 77.2 (7.1) |
| 5.0 | 5.0 | 75, forward | 97.4 (0.7) | 92.3 (4.0) |

Table 5 shows the decrease in standard deviation of creep retention across multiple set-up conditions using 30 mg/m Ex3 formulation per strand at 1200 ft/min. The first set of condition display an applicator head tilt of 90° with varying deflection levels. The non-deflection condition showed the lowest creep retention as well as high standard deviations. When beginning to introduce deflection (2.5°) in formulation Ex3, first the creep retention increases (over no deflection conditions). As the degree of deflection increases (5.0°) the creep retention continues to increase and the standard deviation decreases; leading to more consistent products. The same holds true for condition values at the 75° applicator head tilt (Table 5).

Whether dealing with heterophasic polyolefin-based formulations or APAO-dominated formulations, it is imperative to consider the deflection angle (entrance and exit) when using an applicator such as the Allegro™ nozzle available from Nordson Corp. This invention demonstrates that small adjustments to the line configuration can drastically increase end performance of an adhesive composition without any adjustment to the formulation. It further can allow for lower standard deviation during the run process and facilitate using lower coat weights without compromising end performance.

When switching from SBc to polyolefin-based formulations, particularly those based on heterophasic polyolefins, not only did the adhesives coat well with the downward force on the elastic strand (deflection), but it was found that this change in configuration could drastically improve end creep performance and overall consistency. As described above, several formulations were tested at set deflection values to fully capture this important finding.

Comparative Example 1

Comparative Example 1 was run to assess the effect of deflection on an SBc-based formulation. The SBc-based formulation was run at a line speed of 500 m/min with a coat weight of 25 mg adhesive/m strand at an open time of 0.15 seconds using 40 psi nip compression. Substrates utilized during fabrication include a breathable polyethylene film as the primary substrate, 680 dtex Invista elastic strands (3 strands at 5 mm spacing elongated at 300% during application), and 15 gsm nonwoven as the secondary substrate. The distance from inlet strand guide to applicator head was the same as the distance from the applicator head to the first outlet idler and was approximately equal to 3.5". In this case, values for both the entrance angle (inlet strand guide to applicator head) and exit angle (applicator head to first outlet idler) are identical.

TABLE 6

| Entrance Angle, ° | Exit Angle, ° | Initial Retention, % | 1 Wk Aged Retention, % | 4 Wk Aged Retention, % |
|---|---|---|---|---|
| 0.0 | 0.0 | 89.5 (9.3) | 85.1 (9.2) | 87.3 (6.4) |
| 2.5 | 2.5 | 95.8 (0.8) | 93.0 (2.2) | 93.0 (2.7) |
| 5.0 | 5.0 | 92.6 (5.3) | 93.6 (3.5) | 95.3 (1.3) |

The data above in Table 6 represents the results when using a SBc-based formulation, in particular, one containing a SBS (styrene-butadiene-styrene) block copolymer. The formulation further contains at least one tackifying resin, a plasticizer, and an antioxidant. The creep retention values appear to improve slightly overall with deflection, but the pattern of adhesive formed on the substrates tends to be unpredictable. In particular, deflection used with this SBc-based formulation resulted in the adhesive agglomerating along the lamination, providing an uneven coating. These areas with higher concentration of adhesive can lead to improved creep retention despite the uneven pattern appearance. Moreover, such an uneven spray and adhesion pattern would be unacceptable at a commercial scale.

Comparative Example 2

Comparative Example 2 was run to assess the effect of deflection on another SBc-based formulation. The SBc-based formulation was run at a line speed of 900 ft/min with a coat weight of 30 mg adhesive/m strand at an open time of 0.15 seconds using 40 psi nip compression. Substrates utilized during fabrication include a non-breathable polyethylene film as the secondary substrate, 680 dtex Invista elastic strands (3 strands at 5 mm spacing elongated at 300% during application), and 15 gsm nonwoven as the secondary substrate. The distance from inlet strand guide to applicator head was the same as the distance from the applicator head to the first outlet idler and was approximately equal to 3.5". In this case, values for both the entrance angle (inlet strand guide to applicator head) and exit angle (applicator head to first outlet idler) are identical.

TABLE 7

| Entrance Angle, ° | Exit Angle, ° | Initial Retention, % | 1 Wk Aged Retention, % | 4 Wk Aged Retention, % |
|---|---|---|---|---|
| 0.0 | 0.0 | 95.7 (3.9) | 92.8 (2.4) | 95.4 (1.2) |
| 2.5 | 2.5 | 97.2 (0.3) | 94.7 (1.4) | 95.4 (1.6) |
| 5.0 | 5.0 | 95.9 (1.9) | 92.5 (3.1) | 92.4 (2.1) |

The data above in Table 7 represents the results when using a SBc-based formulation, in particular, one containing a styrene-isoprene-styrene (SIS) triblock/styrene-isoprene (SI) diblock copolymer blend. The formulation further contains at least one tackifying resin, a plasticizer, and an antioxidant. In this Comparative Example 2, the creep retention performance of the SBc-based formulation was not shown to be dependent on deflection. For example, the four-week creep retention data of the formulation not subject to any deflection performed either the same as or better than the formulation subject to exit and entrance angles of 2.5° or 5.0°.

Within this specification embodiments have been described in a way which enables a clear and concise specification to be written, but it is intended and will be appreciated that embodiments may be variously combined or separated without parting from the invention. For example, it will be appreciated that all preferred features described herein are applicable to all aspect of the invention described herein.

What is claimed:

1. A method of using a polyolefin-based, hot melt adhesive comprising the steps of:
   applying the adhesive in a molten state with an applicator to a primary substrate comprising an elastic strand, wherein: an exit angle defined by a line normal to the axis of a neutrally-positioned applicator and the elastic strand extending from the applicator in the downstream direction of travel is at least 2.5°; and an entrance angle defined by a line normal to the axis of a neutrally-positioned applicator and the elastic strand extending from the point of contact of the applicator tip with the elastic strand in the upstream direction of travel is at least 1°;
   bonding a secondary substrate to the primary substrate by contacting the secondary substrate with the adhesive, wherein the applicator has an applicator tip adapted to apply the adhesive directly to the primary substrate at a point of contact and to create a downward force on the primary substrate at the point of contact.

2. The method of claim 1, wherein the exit angle is between 2.5° and 20°.

3. The method of claim 2, wherein the exit angle is between 2.5° and 10°.

4. The method of claim 3, wherein the exit angle is between 2.5° and 7.5°.

5. The method of claim 1, wherein the entrance angle is between 1° and 20°.

6. The method of claim 5, wherein the entrance angle is between 2° and 10°.

7. The method of claim 6, wherein the entrance angle is between 2.5° and 7.5°.

8. The method of claim 1, wherein, during the applying step, a head tilt angle defined by a line tangent to the point of contact of the strand and the applicator tip and an axial line extending along the direction of travel of the adhesive as it exits the applicator is between 60° and 89° or is between 91° and 120°.

9. The method of claim 8, wherein the head tilt angle is between 70° and 88°.

10. The method of claim 9, wherein the head tilt angle is between 80° and 88°.

11. The method of claim 1, wherein the adhesive comprises a polymer component, a plasticizer, a tackifying resin and an antioxidant package, and the polymer component comprises a polyolefin.

12. The method of claim 11, wherein the polymer component comprises at least 50% by weight of said polyolefin.

13. The method of claim 1, wherein the adhesive comprises a polymer component, a plasticizer, a tackifying resin and an antioxidant package, and the polymer component consists essentially of a polyolefin or a blend of polyolefins.

14. A method of using a polyolefin-based, hot melt adhesive comprising the steps of:
   applying the adhesive in a molten state with an applicator to an elastic strand, wherein: an exit angle defined by a line normal to the axis of a neutrally-positioned applicator and the elastic strand extending from the applicator in the downstream direction of travel is at least 2.5°; and an entrance angle defined by a line normal to the axis of a neutrally-positioned applicator and the elastic strand extending from the point of contact of the applicator tip with the elastic strand in the upstream direction of travel is at least 1°; and
   bonding a secondary substrate to the elastic strand by contacting the secondary substrate with the adhesive, wherein the applicator has an applicator tip adapted to apply the adhesive directly to the elastic strand at a point of contact and to create a downward force on the elastic strand at the point of contact.

* * * * *